United States Patent [19]
Swanson et al.

[11] Patent Number: 5,956,355
[45] Date of Patent: Sep. 21, 1999

[54] METHOD AND APPARATUS FOR PERFORMING OPTICAL MEASUREMENTS USING A RAPIDLY FREQUENCY-TUNED LASER

[75] Inventors: Eric A. Swanson, Acton; Stephen R. Chinn, Westford, both of Mass.

[73] Assignee: Massachusetts Institute of Technology, Cambrige, Mass.

[21] Appl. No.: 08/877,340

[22] Filed: Jun. 17, 1997

Related U.S. Application Data

[63] Continuation-in-part of application No. 08/607,787, Feb. 27, 1996, which is a continuation-in-part of application No. 08/577,366, Dec. 22, 1995, Pat. No. 5,748,598, application No. 08/252,940, Jun. 2, 1994, abandoned, and application No. 08/916,759, Aug. 19, 1997, Pat. No. 5,784,352, which is a continuation of application No. 08/492,738, Jun. 21, 1997, abandoned, which is a continuation-in-part of application No. 08/033,194, Mar. 16, 1993, Pat. No. 5,459,570, which is a continuation of application No. 07/692,877, Apr. 29, 1991, abandoned

[60] Provisional application No. 60/037,488, Feb. 7, 1997.

[51] Int. Cl.⁶ ..................................................... H01S 3/10
[52] U.S. Cl. ............................................. 372/20; 356/355
[58] Field of Search .................................. 372/20, 32, 92, 372/97; 356/355, 357

[56] References Cited

U.S. PATENT DOCUMENTS

| | | | |
|---|---|---|---|
| 5,161,165 | 11/1992 | Zorabedian | 372/20 |
| 5,333,049 | 7/1994 | Ledger | 356/355 |
| 5,337,144 | 8/1994 | Strul et al. | 356/355 |
| 5,392,308 | 2/1995 | Welch et al. | 372/92 |
| 5,646,731 | 7/1997 | Wickramasinghe et al. | 356/357 |

FOREIGN PATENT DOCUMENTS

| | | |
|---|---|---|
| 0 335 691 | 10/1989 | European Pat. Off. . |
| 0 469 259 A2 | 2/1992 | European Pat. Off. . |
| 2 050 684 | 1/1981 | United Kingdom . |
| WO 95/31694 | 11/1995 | WIPO . |

*Primary Examiner*—Rodney Bovernick
*Assistant Examiner*—Robert E. Wise
*Attorney, Agent, or Firm*—Testa, Hurwitz & Thibeault, LLP

[57] ABSTRACT

An optical system, in one embodiment including an external-cavity frequency-tuned laser having a tunable longitudinal cavity mode and a center tunable wavelength. The external-cavity frequency-tuned laser includes an optical cavity, an optical gain medium positioned within the optical cavity, and a rapid tuning wavelength selecting device positioned to receive light from the optical gain medium and adapted to return selected wavelengths of light to the optical gain medium. The external-cavity frequency-tuned laser is substantially continuously tunable and the tunable wavelength selecting device tunes the center wavelength of the external-cavity frequency-tuned laser at the same rate as the longitudinal cavity mode of the external-cavity frequency-tuned laser is tuned. In another embodiment the optical system includes an interferometer in optical communication with the external-cavity frequency-tuned laser. The interferometer is adapted to project a portion of light from the external-cavity frequency-tuned laser onto a sample, to receive light altered by the sample, and to combine light reflected from the sample and the light from the external-cavity frequency-tuned laser. A detector positioned to receive the combined light from the interferometer and to generate a signal in response thereto. A processing unit in communication with the detector performs digital signal processing to extract spatial information related to the sample in response to the signal from the detector.

13 Claims, 6 Drawing Sheets ns in the source;

METHOD AND APPARATUS FOR PERFORMING OPTICAL MEASUREMENTS USING A RAPIDLY FREQUENCY-TUNED LASER

PRIORITY INFORMATION

This patent application claims priority from U.S. Provisional Application No. 60/037,488, filed on Feb. 7, 1997, herein incorporated by reference.

This application also claims priority as a continuation-in-part application to copending U.S. patent application Ser. No. 08/607,787, filed Feb. 27, 1996, which is a continuation-in-part application of U.S. patent application Ser. No. 08/577,366, filed Dec. 22, 1995, now U.S. Pat. No. 5,748,598, and is a continuation-in-part application of U.S. patent application Ser. No. 08/252,940, filed Jun. 2, 1994, now abandoned, and is also a continuation-in-part application of U.S. patent application Ser. No. 08/916,759, filed Aug. 19, 1997, now issued as U.S. Pat. No. 5,784,352, which is an FWC application of U.S. patent application Ser. No. 08/492,738, filed Jun. 21, 1997, now abandoned, which is a continuation-in-part of U.S. patent application Ser. No. 08/033,194, filed Mar. 16, 1993, now U.S. Pat. No. 5,459,570, which is a continuation of U.S. patent application Ser. No. 07/692,877, filed Apr. 29, 1991, now abandoned.

GOVERNMENT SUPPORT

This invention was made with government support under Contract Number F19628-95-C-0002 awarded by the United States Air Force. The government has certain rights in the invention.

FIELD OF INVENTION

The invention relates to the field of optical imaging and more specifically to the field of interferometric-based optical imaging.

BACKGROUND OF THE INVENTION

Interferometric optical imaging has emerged as a powerful technology for high resolution (~$\mu$m) visualization of microstructural optical properties such as absorption, scattering, loss, birefringence, and spectroscopic analysis. Several embodiments of this imaging technology require a mechanically scanned reference arm. For instance, in optical coherence domain reflectometry (OCDR) a longitudinally scanned reference arm and a broad bandwidth light source are used to create reflectivity profiles of a sample's optical properties. Due to the broad bandwidth of the optical source, as the reference arm mirror is translated, optical interference between reflections from the reference mirror and reflections or scattering sites within the sample, is detected at the photodetector when the respective path lengths are matched to within the source coherence length. Such mechanical scanning can lead to low image acquisition speed, limiting utility in many applications. Techniques based on optical frequency domain reflectometry (OFDR) ideally have no moving parts and thus potentially can scale to high rate imaging. However, today's known OFDR embodiments typically suffer from poor system dynamic range and sensitivity, limited potential imaging speed, and poor linewidth or resolution.

The present invention seeks to overcome these limitations.

SUMMARY OF THE INVENTION

One aspect of the invention relates to an OFDR system for obtaining spatial information about a sample. One embodiment includes an external-cavity frequency-tuned laser. The external-cavity frequency-tuned laser includes an optical gain medium and tuning elements in an external-cavity. The external-cavity includes a wavelength selecting device, positioned to receive light from the optical gain medium and direct light back to the optical gain medium. The wavelength selecting device tunes the center wavelength at the same rate as the longitudinal mode of the external cavity is tuned. In one embodiment the wavelength selecting device includes an optical dispersion device and an angular scanning device positioned to transmit light from the optical gain medium to the dispersion device. The system further includes an interferometer containing the object under study illuminated by the external-cavity frequency-tuned laser, and a detector positioned to receive light from the interferometer and to generate a signal in response thereto. An electronic processing unit is connected to the detector. The processing unit performs digital signal processing to extract spatial information in response to the signal from the detector.

BRIEF DESCRIPTION OF DRAWINGS

The foregoing and other objects, features and advantages of the invention will become apparent from the following more particular description of preferred embodiments of the invention, as illustrated in the accompanying drawings.

FIG. 2a is another embodiment of the external-cavity frequency-tunable laser shown in FIG. 2 with the scanning mirror replaced by a AOTF unit;

DESCRIPTION OF PREFERRED EMBODIMENTS

Figure 1:
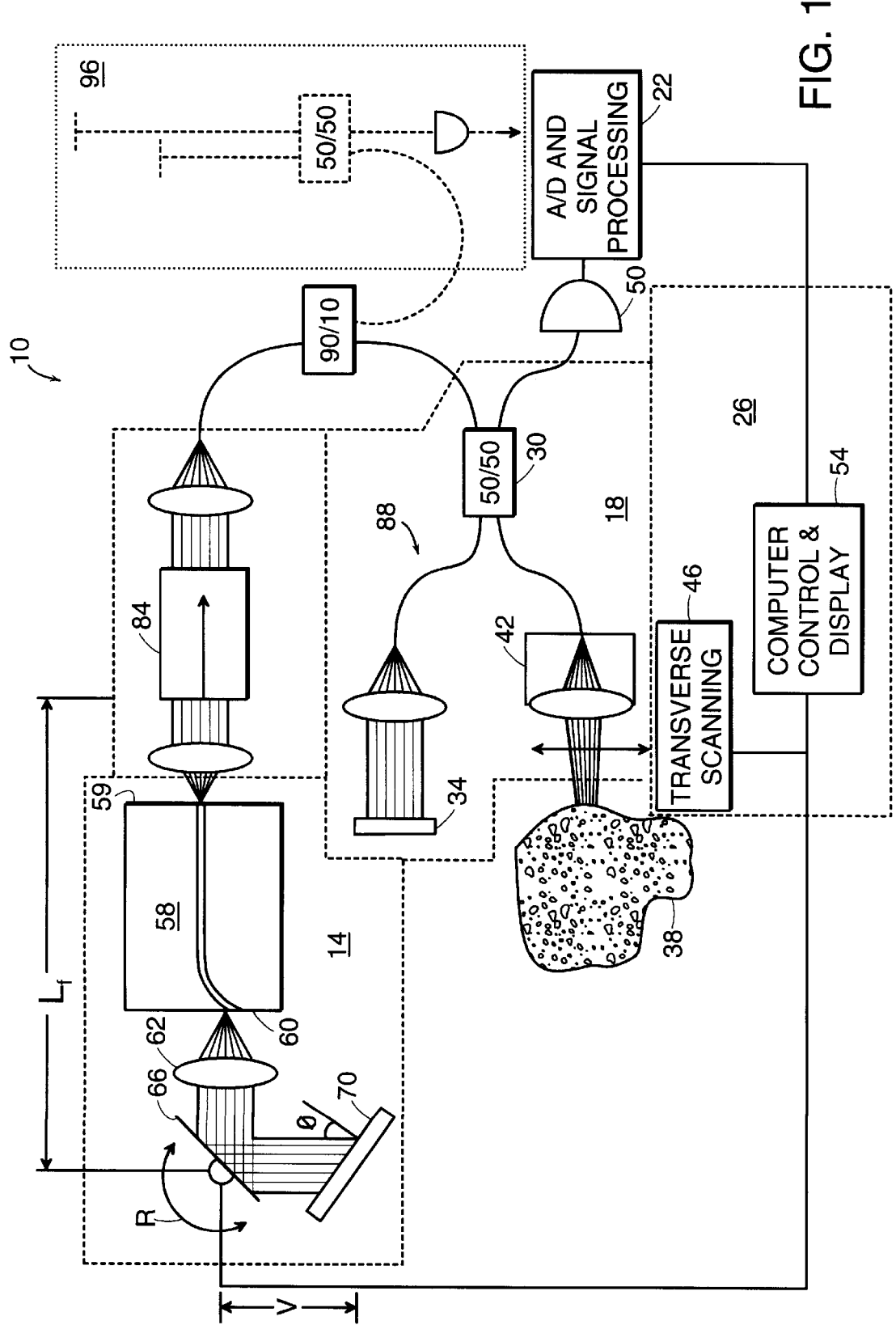
FIG. 1 is a block diagram of an embodiment of the invention with an embodiment of an external-cavity laser.

Referring to FIG. 1, an embodiment of an OCDR system 10 includes an external-cavity frequency-tuned laser 14 which is rapidly and nearly continuously tunable, an interferometer 18, a processing unit 22 and a computer controller and display 26. In the embodiment shown, light from the external-cavity frequency-tuned laser 14 is divided by an optical coupler 30 into two beams. One beam is directed toward a reference mirror 34 and reflected back toward the coupler 30. The second beam is directed toward a sample 38. This light from coupler 30 impinges on the sample 38 by way of translatable probe 42. This probe 42 attached to a transverse scanning device 46 scans the beam across the sample 38. Transverse scanning may be accomplished by a number of means including, but not limited to, moving mirrors, moving lenses, electrooptic deflector, or any other means to accomplish the translation of light across sample 38. In another embodiment the probe 42 is stationary and the sample 38 is moved across the beam. Light reflected by the sample 38 returns to the coupler 30 and combines with light reflected from the reference mirror 34. The recombined beams form an interference pattern which is detected by photodetector 50. A signal generated by the photodetector 50 is digitized and processed by the signal processor 22 and the result displayed on a computer controller and display 54.

An embodiment of the external-cavity frequency-tunable laser shown in FIG. 1 uses a broadbandwidth semiconductor 58 amplifier. Typically, as is known in the art, the ends of the amplifier chip through which the optical beam propagates are facets 59, 60 along the natural crystallographic cleavage planes of the chip. As such, they are parallel to each other. To suppress self-oscillation of the amplifier chip, and to minimize ripple in the spectrum of the external-cavity laser it is important to minimize the reflectivity of the facet 60 interior to the external-cavity by a combination of anti-reflection coating and angling of the single-spatial-mode, narrow-stripe gain region with respect to the facet. Optical gain is provided by injecting current into the narrow stripe region defining the single spatial mode. At the output facet 59 of the external-cavity some small reflectance is required to provide oscillation in an external-cavity mode. The residual reflectance of the angled stripe may suffice if the external coating is appropriate, but it is preferable to have the stripe perpendicular to the output facet.

In one embodiment, an external-cavity laser has portions of the cavity on both sides of the amplifier chip (double-ended external-cavity). In this case both amplifier facet reflectances, one at each end of the chip, must be suppressed. Although a semiconductor laser is shown in this embodiment, other embodiments utilize other optical gain media such as rare-earth doped fibers and other solid state gain media. In the embodiment shown, a light beam exiting from the back facet 60 is collimated by lens 62 and reflected from a steerable mirror 66. Embodiments of the steerable mirror 66 includes a galvanometer, a PZT, an electro-optic beam deflector, or a voice coil driven mirror. The reflected light beam is directed to a wavelength selective element 70. In one embodiment, the wavelength selective element is a ruled grating. The ruled diffraction grating operates in the Littrow configuration, known in the art, which retro-reflects light of a wavelength obeying the diffraction condition determined by the angle of incidence and the grating ruling pitch. In another embodiment a dispersive prism followed by a mirror, as is known in the art, is used.

An external-cavity for laser 14 is formed between the partially reflective surface of the cleaved front facet surface 59 (or alternatively a partially transmissive surface in front of the laser) and the grating 70. By angularly steering (arrow R) the steerable mirror 66, the laser 14 is frequency-tuned. When the relative distance of the laser 58 to mirror 66 spacing, the laser 58 to grating 70 spacing, the grating angle φ, and the grating ruling are properly selected nearly continuous frequency tuning can be accomplished. In an embodiment having a reflection from the tuning mirror 66, a condition exists under which the frequency of a lasing axial cavity mode tunes at approximately the same rate as the grating center frequency thereby avoiding axial mode hop. The condition is approximately given by the expression:

$$V = \frac{L_f}{\tan^2\phi - 1}$$

where V is the distance from mirror 66 to grating 70, $L_f$ is the fixed distance from the rotational axis of mirror 66 to laser front facet reflector 59 and (φ>45°) is the angle of incidence onto the grating at the scan center wavelength measured from a normal to its surface. This method avoids the need of rotating the tuning element around a displaced pivot point to avoid mode hops, as is known in the art. Such designs are limited to slower mechanical scanning methods.

This design criterion neglects dispersive effects, and provides first-order compensation for the axial mode tuning. Under the above spacing condition, there is a parabolic increase in the mode index about the center wavelength. A simple way to approximately compensate for this (and other dispersive effects) is to use a chirped Bragg grating in an optical fiber or optical planar waveguide to provide a quadratic phase shift to its reflected light. The compensation may be exact if a constant second derivative of phase with respect to frequency is used. However, this is a more stringent condition that requires carefully designing a chirped grating. It should be noted that with proper choice of grating length and chirp, nearly perfect mode compensation can be achieved over several percent of optical bandwidth without the stringent grating requirements just discussed.

Figure 2:
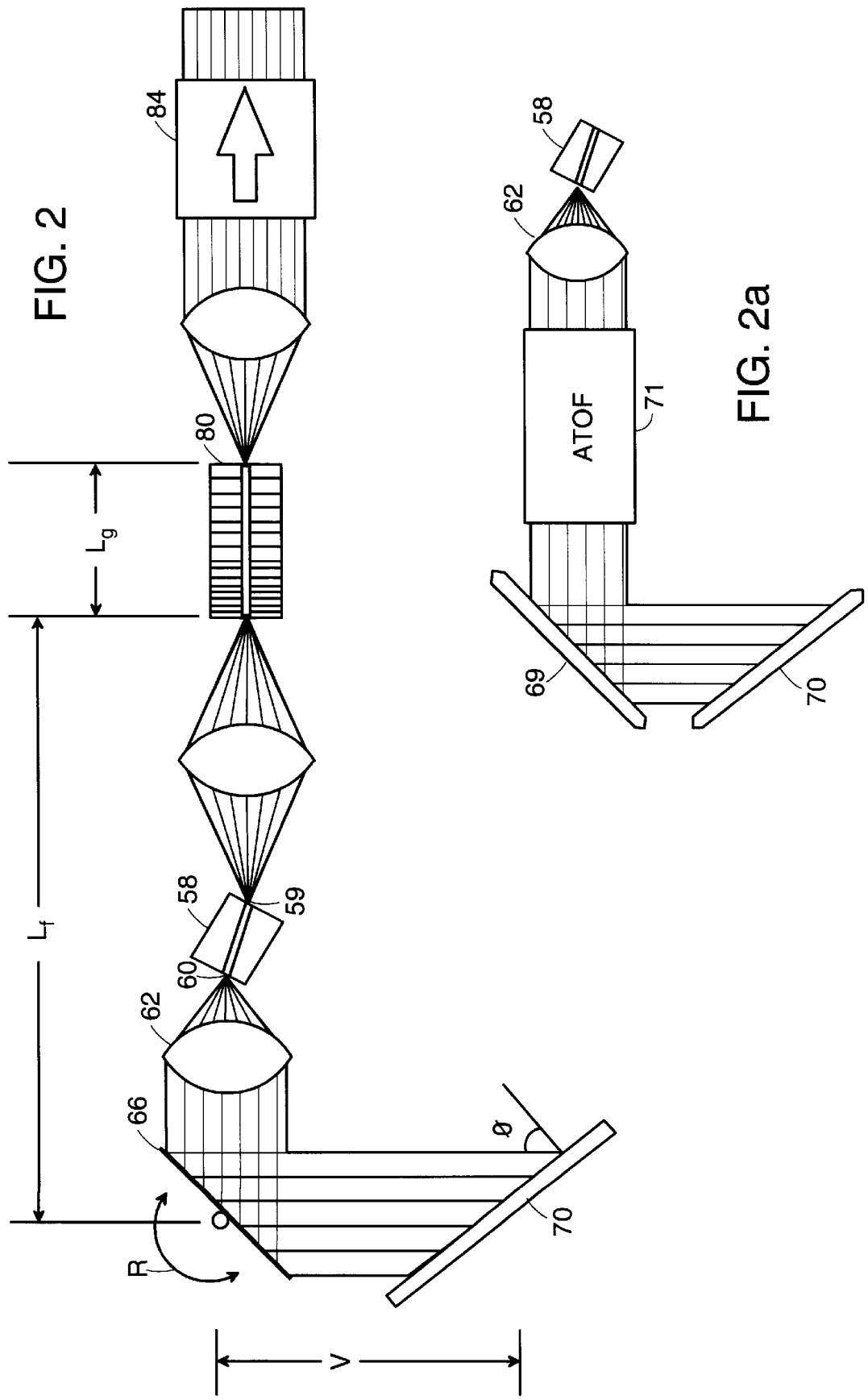
FIG. 2 is an another embodiment of the external-cavity frequency-tunable laser shown in FIG. 1.

One embodiment of such external-cavity frequency-tuned laser using a chirped Bragg grating is shown in FIG. 2. Note that this embodiment is an example of a double-sided external-cavity, with optical elements on either side of the optical gain medium. In this embodiment a Bragg waveguide grating 80 is used as a weak dispersive reflector to reflect light back into the external-cavity. The Bragg waveguide grating 80 is also used as a transmissive output coupler. The rapid scanning Littrow steerable mirror 66 configuration of the previous embodiment is still used for linear frequency compensation, with a slight adjustment of the grating spacings to allow for a fixed component of cavity distance equal to one half the grating optical path length. That is:

$$V = \frac{L_f + n\frac{L_g}{2}}{\tan^2\phi - 1}$$

A mode-hop, or change in mode order, is equivalent to having a different number of wavelengths in the cavity. If the wavelength increases at the same rate as the total cavity length increases, mode hops are not present. In the embodiment of FIG. 1, both the wavelength and the cavity length change with tuning angle of mirror 66. The previous equation defined a condition at which both the cavity length and retro-reflected wavelength tune with the same linear rate at the center of the tuning range. This tuning has non-linear, primarily quadratic, components that cause the cavity length and wavelength changes to diverge on either side of the center of the tuning range. This divergence is referred to as a second-order deviation to the continuous tuning condition. The second-order correction condition, which if satisfied greatly extends the length range of non-mode hopping, is defined by:

$$V = \left(\frac{f_0 n L_g}{f_r - f_l}\right)\frac{1}{\tan^2\phi(1 + \tan^2\phi)}$$

where n is the average refractive index of the chirped Bragg grating, $f_0$ is the center optical frequency (and the Bragg frequency at the center of the grating), $f_r - f_l$ is the chirp of the Bragg frequency across the grating (greater than or equal to the desired frequency sweep), and $L_g$ is the Bragg grating length. In practice, with fixed Bragg grating parameters, the distances V and $L_f$ are experimentally adjusted near their nominal values for exact second and first order compensation, respectively. The fixed length $L_f$ in this embodiment is the fixed optical path length of the cavity that does not change with tuning conditions, extending from the center of the tuning mirror, through the collimating lenses and amplifier, to the interior side of the Bragg grating.

The remarkable feature of this mode compensation is that it results in an extremely large cavity spectral mode separation, limited only by higher order or other uncorrected dispersive effects. This means that maintaining very short cavity dimensions is not required to provide few modes within the grating resolution envelope.

In one embodiment, an AOTF is used to replace the mechanically-scanned tuning mirror 66 of the embodiment of the external-cavity frequency-tunable laser shown in FIG. 2. In this embodiment, the scanning mirror 66 is replaced by a fixed diffraction grating 69. The AOTF 71 is inserted in the collimated beam between the lens 62 and grating 69. When the wavelength of the transmitted beam is changed by tuning the AOTF 71, which is designed to impart no angular deviation to the beam as the AOTF is tuned, the diffraction angle from the grating 69 changes. The changing diffraction angle causes a path length change in the beam retroreflected from the second Littrow grating 70 similar to that of the scanned mirror embodiment. The AOTF imparts a small optical frequency shift to the beam transmitted in one direction, but the frequency shift is reversed in the opposite direction, so that a beam propagating through a round trip in the cavity suffers no cumulative radio-frequency shifts.

In more detail and referring again to FIG. 1, the output of the laser is sent into a Faraday isolator 84 and coupled into a fiber optic Michelson interferometer 18. In one embodiment the interferometer is constructed with angled fiber facets (not shown). The isolator 84 and angled fiber facets (typically>6°) serve to minimize reflections which can detrimentally effect the laser stability.

One arm 88 of the interferometer leads to the reference mirror 34, the other to the probe module 47 that couples light to and from the sample 38 and performs transverse scanning 46. Although in the embodiment shown the probe module 47 is scanned, alternatively in another embodiment the sample 38 is scanned laterally by translating the sample 38 perpendicular to the axis of the probe module 42 using linear translation stages or angular scanning devices as is known in the art. The light reflected from the reference mirror 34 and the sample 38 are recombined by the beam splitter 30 and passed to the photodetector 50. Although a single photodetector is shown, in another embodiment, double balanced detection is used as is known in the art, to cancel excess intensity noise from the source and sample-sample beat signals. In this Embodiment the interformeter is modified from simple Michaelson interferometer as is known in the art. The signal generated by the photodetector 50 in response to the combined reflected light is amplified, filtered and converted to a digital signal by an A/D converter and digitally processed by processor 22. Alternatively analog signal processing techniques could be used as is known in the art.

When the angle (R) of the steerable mirror 60 is scanned in a saw-tooth pattern, the system 10 operates as a normal OFDR system with the added improvement of a nearly continuous frequency sweep as described in detail above. One embodiment of the device of FIG. 2 (without the chirped Bragg grating) operated with a greater than 20 nm tuning range at 840 nm center frequency. Because the grating frequency does not vary linearly with mirror angle (R) (its wavelength tunes in a slightly non-linear manner with respect to incident angle), there is a slight frequency sweep non-linearity of the output spectrum that leads to decreased resolution. That is, the output frequency is not exactly linear in time and thus the beat frequencies between the reference reflector and a reflection from the sample will not be constant in time. The effects of such a non-linearity can be eliminated with post detection processing as described below or by altering (pre-distorting) the form of the scan from a saw tooth pattern.

The use of mechanical scanning systems results in some difficulty in achieving very high scan speeds (e.g. video rates) and a linear frequency chirp. For example, in AOTF systems the transit time of the acoustic wave from the tuning transducer of the AOTF limits the available tuning speed, while in systems using a grating 70 and a steerable mirror 60, the inertia of the steerable mirror 60 limits tuning speed. Typical galvanometers will not reproduce, with good fidelity, a sawtooth waveform with a frequency of higher than about 50 Hz. However, such galvanometers can be driven with pure sinusoidal signals at frequencies much higher. Normal and mechanically-resonant galvanometers can be driven at video rates (~15 kHz) using a pure sinusoid. In other embodiments, combinations of scanning mechanisms and frequency dispersive elements are used to achieve very high rate tunable optical filters with a sinusoidal sweep pattern.

In other embodiments, rotating polygons, electro-optic beam deflectors, and tunable fiber Fabry Perot filters may be used with frequency dispersive elements to achieve high scanning rates, instead of the galvanometer and grating described above. In the embodiment shown in FIG. 1, if the steerable mirror is a resonant galvanometer driven by a sinusoidal waveform, high speed -sinusoidal tuning of the laser frequency can be achieved. In order to correct for non-linear frequency sweep and ensure proper demodulation of the reflectance profile of the sample 38 an auxiliary interferometer 96 in one embodiment (shown in phantom) is used to sample the signal produced by the photo-detector 50 at equal increments of the source frequency, as is known in the art. The auxiliary interferometer 96, corrects for any non-linearity in frequency sweep by sampling the detected signal at equally spaced source frequency increments as is well known in the art. In yet another embodiment to mitigate the effects of source intensity fluctuations during the frequency sweep a separate calibration photodetector is incorporated to measure the laser output power and used to adjust power of laser 14 or used to normalize the digitized signal in processing unit 22. Although the approach of using an auxiliary interferometer 96 can partially correct for deviations from the ideal in the sweep of the optical source by providing signal trigger pulses at equally spaced increments in the source frequency, such approaches have several limitations, including hardware complexity and system performance limitations due to instabilities in the auxiliary interferometer 96 paths and processing electronics.

Figure 3:
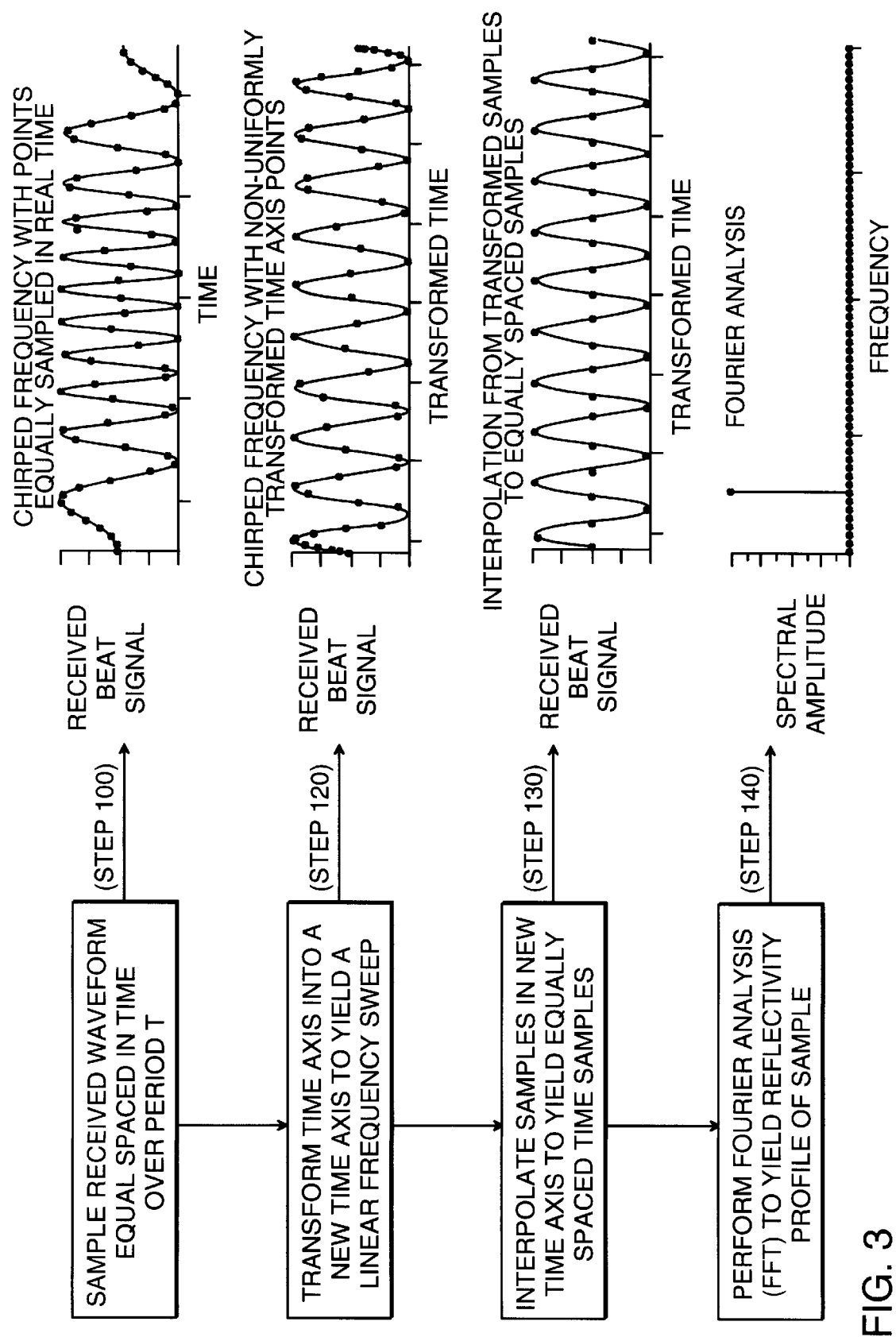
FIG. 3 is an embodiment of a non-linear signal processing algorithm to compensate for non-linear frequency sweeps in the source.

Therefore, in another embodiment, in which the frequency sweep is non-linear but is very repeatable, correction for deviations from the ideal in the sweep of the optical source, is performed by the signal processing of the detector signal. Referring to FIG. 3, a flow diagram of an embodiment of a simplified version of the signal processing algorithm is shown. In this embodiment a portion of the periodic signal waveform generated by the detector 50 is sampled over a monotonically increasing or decreasing period T at equally spaced time intervals using a precision clock (STEP 100). Non-uniform time samples could also be used. Next, based on knowledge of the precise shape of the frequency sweep obtained from other means, either known a priori or measured as described below, the time axis is transformed to yield a beat signal characteristic of a linear frequency sweep with a transferred time axis (STEP 120). Once the new time axis is derived, several methods exist to process the data. In one embodiment, the new time samples are interpolated, with equal time increments in the new time axis coordinates, based on a linear or non-linear fit to the actual data values in the new time axis (STEP 130). Then standard Fourier analysis techniques such as the Fast Fourier Transform (FFT) are performed to obtain the reflectivity profile (STEP 140). Other algorithms to obtain the reflectivity profile, such as maximum entropy and wavelet transforms, can also be used.

To understand the basis for the signal processing, let the electric field of the light emitted by the tunable laser be described by the expression:

$$E_o(t) = A(t)\text{Exp}(j(\omega_o t + \phi(t))) \tag{1}$$

where $A(t)$ is the amplitude of the electric field, $\omega_o$ is the nominal center optical frequency, t is time, and $\phi(t)$ is the phase of the electric field. In general, $\phi(t)$, which describes the modulation of the optical carrier phase and frequency, includes a stochastic random phase component which is neglected for the purposes of this description. Assuming that $A(t)$ is a constant, or alternatively that any power fluctuations of the source can be normalized by monitoring the output power of the laser source as previously described, the detected photocurrent is proportional to the squared sum of the electric field reflected from the reference reflector 34, $E_r(t)$, and the reflected field from the sample 38, $E_s(t-\tau)$, as given by the expression:

$$I(t) \sim |E_r(t) + E_s(t-\tau)|^2 \tag{2}$$

where $\tau$ is the relative delay between the reference reflection and the sample reflection and $\tau$ is proportional to the relative distance into the sample 38.

The signal component of interest will consist of the cross term $E_r(t) \cdot E_s(t-\tau)$. Other terms give rise to DC components and signal-signal beat terms which can be removed by signal processing techniques as known in the art or by carefully selecting a nominal time delay between the sample and the reference so that the cross product of the signal and the signal beat noise does not spectrally interfere with the cross product of the reference and the signal spectrum. $E_r(t)$ is just a delayed and scaled version of $E_o(t)$ while, for a single reflection within the sample, $E_s(t-\tau)$ is the product of a scaled and delayed version of $E_o(t)$ times the sample reflection coefficient $r_o \text{Exp}(j\phi_r)$, where $r_o$ and $\phi_r$ are the magnitude and phase of the reflection at $\tau$, respectively. This assumes a single reflection from the sample. Thus, by ignoring the relatively unimportant delay terms and constants, the beat signal of interest at the photodetector 50 output, s(t), is given by the expression:

$$s(t) = r_o \cos(\omega_o \tau + \phi_r + \phi(t) - \phi(t-\tau)) \tag{3}$$

$$= r_o \cos(\omega_o \tau + \phi_r + 2\pi \int dx f(x)) x = \{t-\tau, t\} \tag{4}$$

where $f(t)$ is the modulated optical frequency about the optical carrier center frequency, $f_o = \omega_o/2\pi$. $s(t)$ can be further simplified when $f(x)$ is approximately constant over $\tau$, which is accurate for most of the applications of interest, to:

$$s(t) \approx r_o \cos(\omega_o \tau + \phi_r + 2\pi f(t-\tau/2)\tau)) \tag{5}$$

This can be further simplified to:

$$s(t) \approx r_o \cos(\omega_o \tau + \phi_r + 2\pi f(t)\tau) \tag{6}$$

For the case of an ideal linear chirp of magnitude $\Delta f$ and duration $T_o$, $\phi(t)$ and $s(t)$ are given by the expressions:

$$\phi(t) = (\Delta f/T_o)t \tag{7}$$

$$s(t) = r_o \cos(\omega_o \tau + \phi_r + 2\pi(\Delta f/T_o)\tau t) \tag{8}$$

This can be recognized as a simple sinusoid of magnitude, $r_o$, and frequency $f_b = \Delta f(\tau/T_o)$. Thus by performing appropriate windowing and Fourier analysis $r_o$, and $f_b$, can be determined. From $f_b$, $\tau$ can be determined, and from $\tau$ the relative location of the sample reflection $\Delta x \sim c \tau/2n$ can be determined, where c is the speed of light and n is the group index of refraction. Thus the sample reflection magnitude and location can be identified for this simple case of an ideal linear chirp.

For the case of a sinusoidal frequency sweep, f(t) and s(t) are given by the expression:

$$f(t) = (\Delta f/2) \sin(\omega_m t) \tag{9}$$

$$s(t) = r_o \cos(\omega_o \tau + \phi_r + 2\pi(\Delta f/2)\tau \sin(\omega_m t)) \tag{10}$$

where $f_m = \omega_m/2\pi$ is the modulation frequency and $T_m = 1/f_m$ is the modulation period. This can be recognized as a sinusoidal frequency chirp of the beat signal. Although simple Fourier analysis can not be used to derive $r_o$ and $\tau$, if the time axis is transformed, as described above, using $t_{new} = (1/\omega_m) \sin(\omega_m t)$ and the periodic modulation broken into alternate monotonically increasing and decreasing sections so that the time axis has a one-to-one mapping then $s(t_{new})$ is given by the expression:

$$S(t_{new}) = r_o \cos(\omega_o \tau + \phi_r + 2\pi(\Delta f/T_m)\tau t_{new}) \tag{11}$$

Equation 11 is functionally similar to equation 8 and thus standard Fourier analysis can be performed to derive $r_o$ and $\tau$. Since the time samples in equation 11 are not equally spaced, interpolated values of time and s(t) will generally have to be calculated before standard FFT algorithms can be applied. However other algorithms such as maximum entropy and wavelet transforms can be used for spectral estimation.

In the general case, the frequency sweep, f(t), will be periodic and can be broken up into monotonically increasing or decreasing segments where one-to-one mappings between frequency and time exist. In sections where f(t) changes from an increasing to a decreasing segment (or vise versa) it may be necessary to perform a windowing function to remove data which may not be of high fidelity during transitions. In this case, each segment will contain information about one axial reflectivity profile. By defining a time transformation to be:

$$t_{new} = (T_o/\Delta f)f(t) \tag{12}$$

then $$S(t_{new}) = r_o \cos(\omega_o \tau + \phi_r + 2\pi(\Delta f/T_o)\tau t_{new}) \tag{13}$$

Again this is similar to equation 10 and Fourier or other analysis can be applied to determine the reflection coefficient magnitude and location. In this new coordinate system the samples will not be equally spaced in time as mentioned above, but in one embodiment, new equally spaced time samples are interpolated from the original time samples and then standard windowing and Fourier analysis is applied to derive $r_o$ and $\tau$ or equivalently $r_o$ and $\Delta x$. Further, although an approximate mathematical analysis was performed for a single sample reflection, the more general case of multiple reflections or a continuum of reflections may be treated as a superposition. Thus this analysis and algorithm are directly extendible to arbitrary sample reflectivity profiles. This embodiment of the invention corrects non-linear frequency sweeps using uniform (or non-uniform) time samples and real-time or a priori knowledge of the source frequency sweep profile by relying on non-linear signal processing techniques.

Knowledge of the shape of the frequency sweep required by this embodiment of the algorithmic approach can be obtained from the laser input if the behavior of the laser is well known. For example in a semiconductor laser where the frequency modulation response to current injection is known, then the laser frequency output is derivable from its input. In situations where the behavior is more complicated then optical calibration techniques can be used. For example one can use a calibrated narrowband optical filter (calibrated using a wavemeter for example) and time gating techniques to measure the relative time when the OFDR source frequency passes through the filter. By stepping the filter sequentially through the range of f(t), f(t) can be mapped out. Similarly one can use a laser of known frequency (using again a wavemeter) and perform gating using heterodyne techniques. Also various types of optical delay-lines and optical frequency discriminators (e.g. etalons, Fabry Perots, unbalanced Mach-Zehnder and Michelson interferometers) can be used to determine f(t).

In many cases the OFDR system itself can be used for calibration. If the sample is replaced with a simple and known reflection profile (e.g. a partially reflecting mirror) then with appropriate signal power normalization, the modulated frequency f(t) is contained in s(t) from, for example, equation 6. Using known curve fitting algorithms, f(t) can be derived since most of the parameters either are known (e.g. $\omega_o$, $\tau$, $\phi_r$, $T_o$) or can be derived by other means.

In one embodiment, with sufficient signal processing power and laser stability, f(t) is calibrated in real-time. Since calibration of f(t) can be determined in the manner described (or other techniques as is known in the art) then by placing a reference reflector (not shown) in the sample arm 88 one can perform calibration on a scan-to-scan basis increasing the accuracy of the reflectometry or imaging system. In such an embodiment it is important that the location of the reference reflector be such that the beat frequencies do not lie in a region that contains signals or otherwise interfere with the signal data collection. An alternative to placing the reference reflector in the sample arm is to have the transverse scanning mechanism 46 point to a reference reflector periodically.

Figure 4:
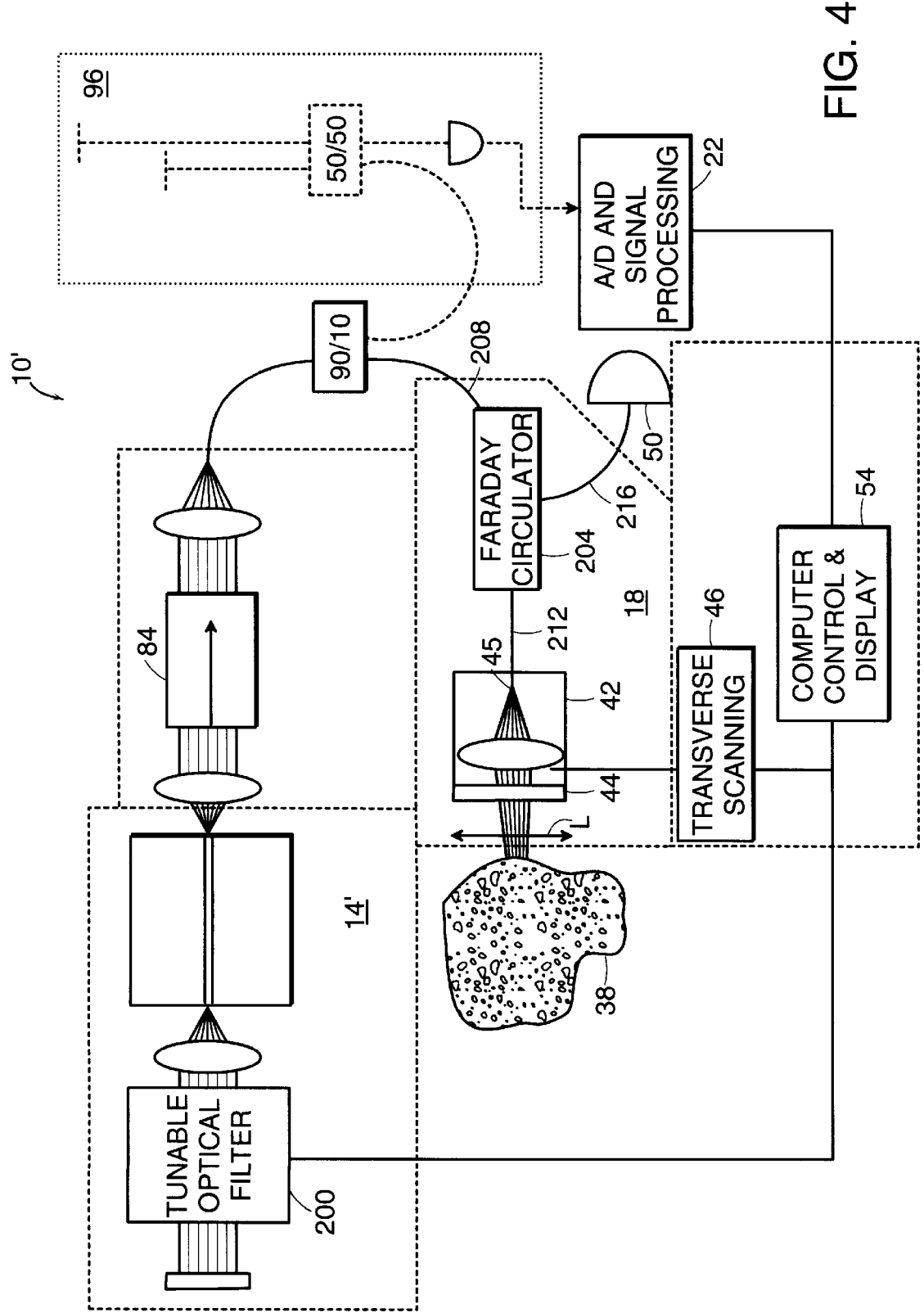
FIG. 4 is another embodiment of the invention using a tunable optical filter.

Referring now to FIG. 4 an alternate embodiment of the system uses an acousto-optic tunable filter 200 (AOTF) as a frequency tuning element. The AOTF 200 has the desirable property that it has no moving parts. An AOTF configured in a double pass geometry can produce an output frequency equal to the input frequency, a necessary condition for single-frequency operation. Ordinarily, the poorer frequency resolution of an AOTF, plus the uncompensated nature of the cavity shown in FIG. 4 would lead to mode hopping. However, in a manner analogous to the cavity design discussed above, a pair of gratings in a pulse compression/dispersion compensation geometry inserted in the cavity provides a large degree of increased cavity mode separation and mode hop suppression. The embodiment shown includes an alternate embodiment of the interferometer 18 utilizing a Faraday circulator 204.

In this interferometer embodiment the laser source 141 is coupled into a first port 208 of a Faraday circulator 204. Light is passed from a second port of the Faraday circulator 212 where it is directed to a probe module 42. The probe module 42 couples light to and from the sample 38 of interest and performs lateral scanning (Arrow L). In addition the probe module 42, in this embodiment, includes a reference reflection reflector 44. In one embodiment, the reference reflector 44 is a partially transmissive beam splitter (e.g. 10%). In another embodiment the reference reflector is flat cleaved output end 45 of fiber 212. Reflected light from the reference and sample 38 are coupled back to the Faraday circulator 204 and directed to the third port 216 of the Faraday circulator 204 where the light is guided to the photodetector 50 and the output signal processed by the processing unit 22. The magnitude of the reference reflection is made as small as possible but sufficient to achieved shot-noise limited operation in the receiver as is known in the art. Ideally, this interferometeric approach can be more than 3 dB more efficient than the approach shown in FIG. 1 since no signal power is lost by being transmitted back toward the source by the coupler 30. Further, the reference reflection magnitude can be tailored to be as small as is practical. The Faraday circulator 204 also helps to further isolate the laser source 141 from stray reflections.

Figure 5:
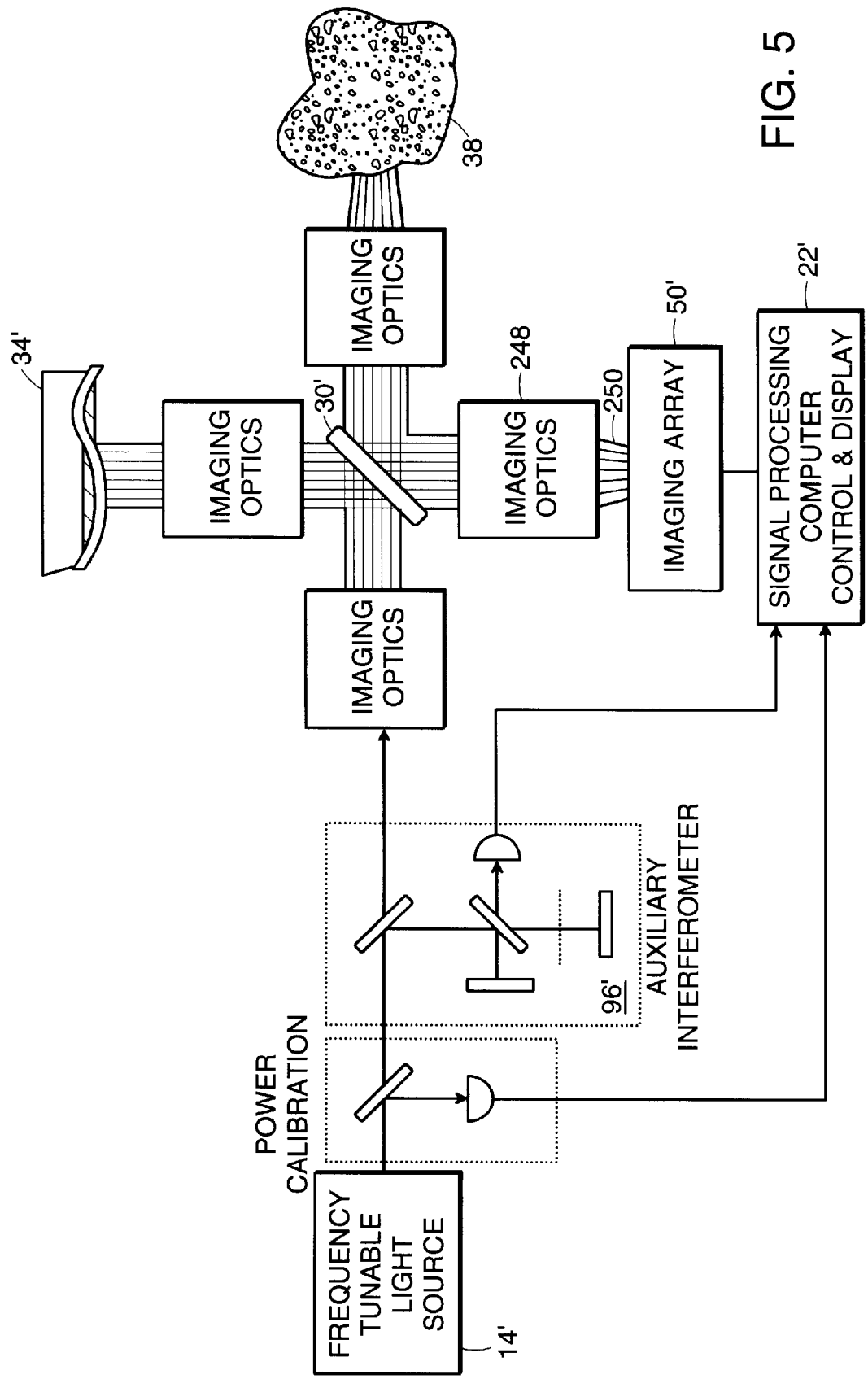
FIG. 5 is yet another embodiment of the invention which is capable of producing images in multiple dimensions.

Most of the embodiments described rely on a serial acquisition of data in which sequential longitudinal reflectivity profiles are collected using the OFDR ranging algorithms and techniques described above. In other embodiments, each reflectivity profile is interlaced with transverse scanning to produce a 2 or 3 dimensional image. However, direct acquisition of multiple longitudinal reflectivity profiles can be collected using an array detector as shown in the embodiment depicted in FIG. 5. In this embodiment the reference mirror 34 may have any surface shape, from a simple planar mirror or a more complex 3-dimensional shape matched to the curvature of the sample 38 to optimize the data collection. The detector array 50 is a one-or two-dimensional array. A one-dimensional embodiment of the array 50 can facilitate the capture of two-dimensional images. The imaging optics 248 in such an embodiment would image a line in the sample 38 using anamorphic optics or cylindrical optics with appropriate lateral resolution and depth-of-field. The height of the line is selected for the application of interest. The imaging optics 248 in the detector arm 250 magnify or demagnify the source image to map into the particular detector geometry. Similarly, a two-dimensional embodiment of the array permits three-dimensional images to be acquired and the optics in such an embodiment map a transverse area of the sample into the transverse area of the detector 50. The imaging optics also map out the appropriate depth-of-field in the sample. That is, the longitudinal (or depth into the sample) distance that the OFDR system images over will be determined in part by the depth of field or confocal parameter of the imaging optics used to image into the sample. In such embodiments appropriate area detectors include line and area CCD's (preferably with frame store areas for faster and more sensitive acquisition), PIN photodetector arrays, and CID detectors. By acquiring multiple pixels in parallel using the detector array one can achieve superior resolution within highly scattering objects by taking advantage of the transverse information across the detector plane. For example, a point-reflection within a highly scattering medium will produce a speckle pattern in the detector plane. By coherently combining the light from adjacent pixels the effect of the speckle can be diminished and the resolution improved. Other algorithms can also be adapted to improve the lateral or longitudinal resolution within a sample by performing joint processing on a group or volume (pixels in depth and transverse dimension) of collected OFDR data.

Figure 6:
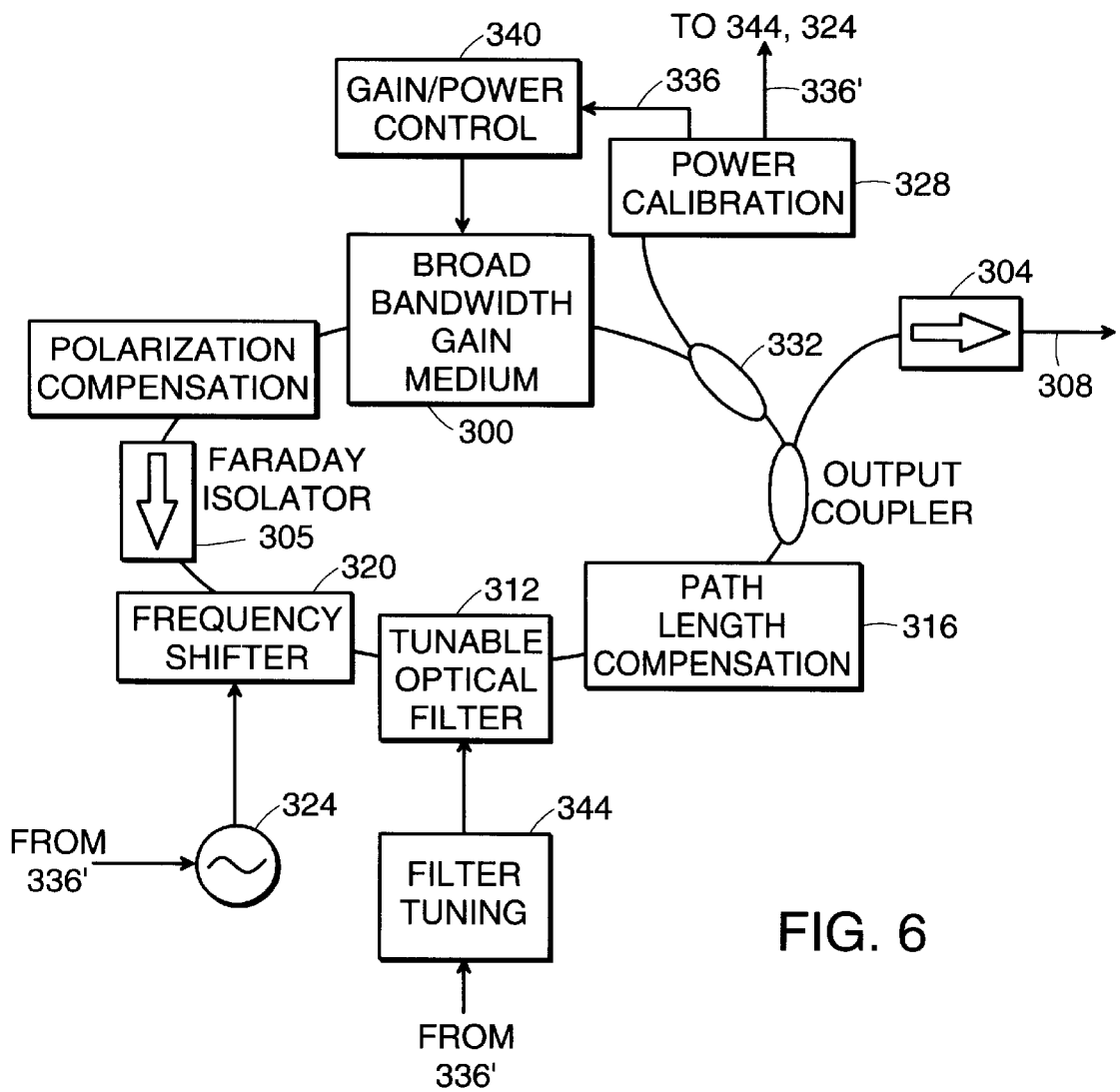
FIG. 6 is another embodiment of the invention in the form of a ring laser.

FIG. 6 shows another embodiment of a tunable laser source as a ring laser that can be used to perform reflectometry and imaging measurements. In this embodiment a fiber ring is shown, although free space embodiments are also possible. In this embodiment the fiber ring includes an optical gain medium (300). In one embodiment the optical gain medium 300 is a semiconductor with angled or appropriately antireflection coated facets to suppress lasing. In a preferred embodiment the gain medium 300 is a rare-earth doped fiber because it is small and readily compatible with fiber ring implementations. In one embodiment the fiber is doped with a dopant such as Yb, Er, Nd, and Tm or a Raman gain medium. Other embodiments include solid state gain media.

In another embodiment, long-period fiber gratings are spliced into the fiber ring so that the optical gain over the laser sweep range is relatively flat and broad. In yet another embodiment a faraday isolator 305 is inserted in the ring to insure unidirectional operation and a faraday isolator 304 is installed at the output 308 to eliminate any feedback into the laser cavity. The ring may be manufactured out of polarization maintaining fiber, single-polarization fiber, or contain fixed or adjustable polarization components.

Every embodiment of the ring laser includes a tunable optical filter 312. In various embodiments this filter may be a fiber Fabry-Perot Filter, acousto-optic tunable filter (AOTF), or tunable mirror/grating as described previously. The tunable filter may be driven in a saw-tooth or triangular fashion (if sufficient tuning bandwidth is available) or a sinusoidal or other drive fashion (if compensated for as described previously).

As described previously, it is important for good dynamic range and sensitivity to eliminate mode-hops and maintain narrow laser linewidth as the laser is tuned. In normal operation, as the optical filter 312 is tuned, the laser will hop into the various cavity modes of the ring. To prevent this, in one embodiment (similar to that described above with respect to FIG. 3), a path length compensation element 316, such as a Fiber Bragg reflector and Faraday circulator or other dispersive or path length compensating element, is included in the ring. As the tunable filter is tuned, this path length compensator 316, which includes an active or passive element, adjusts the total ring optical path length to maintain the lasing condition at the peak of the tunable filter 312. In one embodiment of a fiber ring geometry the path length compensator 316 includes a free space coupling region over which the air gap is adjusted during the filter tuning.

In another embodiment a frequency shifter 320 such as an acousto-optic modulator (AOM), or serrodyne phase modulator (SPM) is inserted into the laser cavity. If an AOM is used, the output frequency and throughput (loss) of the light can be controlled by the frequency and intensity of the radiofrequency drive 324 for the AOM. As is known in the art, if the optical filter 312 is tuned at a rate that equals the frequency shift of the frequency shift element 320 divided by the round-trip propagation delay of the light around the ring then a narrow linewidth frequency sweep will be achieved.

If $f_0'$ is the rate (the prime (') indicating a derivative with respect to time) of tuning of the laser optical frequency, $f_f'$ is the tuning rate of the optical filter 312, c is the speed of light, $f_{Bragg}$ is the frequency shift of frequency shifting element 320, $n_g(\lambda)$ is the effective group index of refraction, $\lambda$ is the instantaneous optical wavelength, and L is the cavity length, then the condition for resonance is approximately given by the expression:

$$f_0'=f_f'=cf_{Bragg}|(n_g(\lambda)L)$$

In this configuration, the output frequency is precisely incremented by an amount equal to the frequency shift imposed by the frequency shifter 320 every time the light circles around the ring. Further, the filter center frequency tuning rate is equal to the frequency shift divided by the round trip propagation time. For example, if the AOM with a Bragg frequency shift of 600 MHz is used as a frequency shifting element 320; a fiber Fabry Perot filter is used as a tunable filter 312; a semiconductor optical amplifier 300 with a bandwidth of 50 nm (~6.25 THz) and center frequency of 1500 nm is used as a gain element; then, assuming a cavity length of ~19.2 m and a group index of refraction of 1.5, the round trip propagation time is ~96 ns. Therefore a bandwidth of 50 nm can be tuned in ~1 ms for a repetition rate of ~1 kHz.

A standard AOM operating as a frequency shifter 320 has a limited optical bandwidth for a fixed input and output angle. There are several alternatives to an AOM to perform such frequency shifting, such as electro-optical modulators. In addition at the expense of additional hardware complexity, autonomous alignment techniques can be implemented and the AOM can be made to work over a broad bandwidth.

In another embodiment an AOTF is used in place of the tunable filter 312, and the frequency shifter 320, combining their functions into one element. By controlling the power level to the AOTF it can also be used for power control either in an open-loop fashion or in response to power calibration unit 328. It should be understood that the AOTF has the disadvantage that tuning the AOTF center wavelength requires that the AOTF radio frequency shift be changed leading to complexities in satisfying the above resonance condition. This limitation can result in mode hops and unacceptable laser linewidth which leads to poor system dynamic range. The mode hops result from the fact that if the filter optical center frequency is swept linearly in time, then the Bragg frequency shift will not be constant as was the case with an AOM, but rather will vary with time. This leads to the inability of the optical filter center frequency to track the laser frequency, resulting in mode hopping.

To overcome this limitation, the path length compensation element 316 (passive or active) adjusts the round trip propagation delay (thereby changing the effective $n_g(\lambda)$ in the above expression) to compensate for the change in Bragg frequency shift. That is, if the Bragg frequency shift must be increased by 1% to tune the AOTF from one end of the optical spectrum to the other, the path length compensation element 316 must increase the round trip propagation time by 1% also. This is accomplished using a passive device such as a Bragg fiber grating and a circulator or by using an active optical delay line such as a fiber stretcher or adjustable free space optical path element.

Another more attractive alternative is to not drive the AOTF filter optical center frequency linearly in time but to alter it so as to cause the optical carrier frequency, which is continuously shifted by AOTF, to track the center frequency of the AOTF. This is accomplished if the equation:

$$\int_{f(t)}^{f(0)} \frac{df}{G(f)} = \frac{t}{T_{rt}}$$

is approximately satisfied. In this equation t is time; f(t) is the instantaneous frequency of the optical field that coincides with the AOTF center frequency; G(f) is the transfer function from the AOTF optical center frequency shift to the Bragg frequency, $f_{Bragg}$ and $T_{rt}$ is the round trip propagation time. Both the AOTF center frequency and instantaneous Bragg frequency shift are functions of time. Although, this equation will ensure a smooth frequency sweep it does not ensure a linear frequency sweep in time.

To a good approximation, the integrand can be expressed as a quadratic function of frequency:

$$\frac{1}{G(f)} \cong a_0 + a_1 f + a_2 f^2$$

This results in the following equation to be solved for $f(t)$:

$$a_0 f(t) + \frac{a_1}{2} f^2(t) + \frac{a_2}{3} f^3(t) = a_0 f(0) + \frac{a_1}{2} f^2(0) + \frac{a_2}{3} f^3(0) - \frac{t}{T_{rt}}$$

From this expression, the corresponding time-dependent radio-frequency drive of the AOTF can be found. In order to extract longitudinal reflectivity profiles of the sample, one embodiment compensates for the non-linear frequency sweep with an auxiliary interferometer or with the signal processing algorithm described previously.

Referring again to FIG. 6, in one embodiment, a power calibration element 328 is used to maintain a known intensity profile of the output waveform (e.g. uniform or raised-cosine). A coupler 332 is used to remove a portion of the output light onto a photodetector which is included in the power calibration element 328. The output of this photodetector is compared to a reference level and the difference 336 is used to adjust the gain 340 of the optical gain medium 300. In other embodiments the difference 336' is used to control the throughput loss of the frequency shifter 320 or optical filter 312. In still another embodiment, the power can simply be monitored and used as an input to the post-detection signal processing unit as described previously.

Although in this embodiment of the ring laser utilization of tunable optical filters 312 and path length compensation elements 316 ensure a nearly continuous frequency sweep, other frequency shifting tunable optical filter elements are used in other embodiments. In one embodiment the Bragg frequency shift of an AOM is adjusted to keep the laser at its resonance condition when a tunable filter Fabry Perot filter, whose center frequency can not be linearly tuned, is used as the tunable optical filter. In another embodiment the filter consists of a cascade of optical filters such as an AOTF and a Fabry Perot filter.

In many applications of interest, the specimen, for example a biological organism, may contain moving objects, for example blood flow, under measurement. The OFDR imaging designs and methods described herein allow the extraction of velocity, position, and magnitude of reflections on a high resolution scale (~10 μm). For an ideal, linearly-chirped OFDR system and a single stationary point target, the detected signal will be a constant frequency sinusoid the magnitude of which is proportional to the reflectivity of the target. Qualitatively, if the target is now moving at a constant velocity then the received signal consists of a chirped frequency sinusoid whose average or nominal frequency will be Doppler upshifted or downshifted depending on the relative motion of the object with respect to measurement system and the rate of the source frequency sweep. Thus by estimating the chirp the actual location of the target along with its velocity is obtained.

For a single target, the instantaneous beat frequency, $f_b$, generated by the OFDR system is approximately given by the equation:

$$f_b = f' \frac{2z}{c} = f_0 \frac{2v}{c} + 2f' \frac{2v}{c} t$$

where $f_0$ is the known starting optical frequency, $f_1$ is the known optical frequency sweep rate from that frequency, z is the unknown target range (with respect to the fixed reference mirror), v is the unknown target velocity (normal to the incident light beam), and c is the speed of light. The first term is a constant frequency proportional to the distance to the target; the second term is proportional to the velocity of the target and is the Doppler component; and the final term is the chirp in the beat frequency which is proportional to the target velocity times the optical frequency sweep scan rate. For multiple targets, the beat signal will consist of the sum of differently weighted multiple beat frequency terms.

There are a variety of algorithms, well known to those skilled in the art of radar analysis, that are utilized to extract Doppler information from the received waveform. The optical technique of the present invention, with its large frequency sweep rate (orders of magnitude larger than in rf or typical optical radar) enables a unique means of extracting Doppler information from a single sweep. A target at a certain distance produces a beat frequency which is proportional to its distance. If the target is moving, a Doppler offset is added to this beat frequency, and this combined beat frequency is broadened (chirped) by the target motion. Neither the range or Doppler offset are known a priori. Further, in many situations there may be multiple targets with different ranges and velocities.

In one embodiment a method of extracting both range and velocity information multiplies the digitized received waveform by a series of dechirping functions having quadratic time-dependent phase factors of the form $\exp(-jKt^2)$, each differing by the proportionality constant K. Each value of K is related to a different Doppler velocity and the known optical frequency scan rate. Each of the series of dechirped waveforms is then Fourier transformed using an FFT or other suitable algorithm. For each chirp parameter, the corresponding Doppler offset is subtracted in the frequency domain from the transformed signal to provide the portion of the beat frequency arising from range. Each target produces a peak signal from a different distinct point in the range-velocity plane. In another embodiment, chirped pulses are sequentially incident onto the target and Doppler information is extracted by processing the reflected light across the multiple pulses, in a manner similar to that of 10.6 μm long-range optical radar.

In another embodiment, range and Doppler information may be extracted using the information contained in a complete cycle of swept frequency, as is known in the art of FM-CW radar systems. In the first half of the scan, if the reference frequency is greater than the delayed return frequency from the target (for relatively large ranges, and smaller Doppler shifts), and in the second part of the scanning cycle where the reference frequency is monotonically decreasing, the reference frequency is less than the delayed return frequency from the target. If the target is stationary, the difference frequency of the interferometric beat signal is the same for both portions of the sweep. If the target is moving, its frequency is Doppler shifted, so that the difference frequency between the reference and delayed Doppler-shifted return frequency from the target will not be the same during two half sweeps. After finding the spectra and corresponding target ranges from the two half-cycles, the mean of the (Doppler shifted) target return positions will give the target position, and the difference between the mean and individual spectra will give the Doppler shift.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An optical system comprising:
   an external-cavity frequency-tuned laser having a tunable longitudinal cavity mode and a center timable wavelength, said external-cavity frequency-tuned laser comprising:
   an optical cavity;
   an optical gain medium positioned within said optical cavity; and
   a rapid tuning wavelength selecting device positioned to receive light from said optical gain medium and adapted to return selected wavelengths of light to said optical gain medium;
   an interferometer in optical communication with said external-cavity frequency-tuned laser, said interferometer adapted to project a portion of light from said external-cavity frequency-tuned laser onto a sample and to receive light altered by said sample, said interferometer adapted to combine light reflected from said sample and said light from said external-cavity frequency-tuned laser;
   a detector positioned to receive said combined light from said interferometer and to generate a signal in response thereto; and
   a processing unit in communication with said detector,
   wherein said external-cavity frequency-tuned laser is substantially continuously tunable,
   wherein said tunable wavelength selecting device tunes the center wavelength of the external-cavity frequency-tuned laser at the same rate as the longitudinal cavity mode of the external-cavity frequency-tuned laser is tuned, and
   wherein said processing unit performs digital signal processing to extract spatial information related to the sample in response to said signal from said detector.

2. The system of claim 1 wherein said wavelength selecting device comprises a grating and an angular scanning device.

3. The system of claim 2 wherein said angular scanning device comprises an electro-optical beam deflector.

4. The system of claim 2 wherein said angular scanning device comprises a rotatable prism.

5. The system of claim 2 wherein said angular scanning device comprises a galvanometer scanned mirror.

6. The system of claim 2 wherein said angular scanning device comprises a resonant scanning mechanism.

7. The system of claim 2 wherein said angular scanning device scans so as to generate a temporally non-linear frequency sweep.

8. The system of claim 7 further comprising:
   an auxiliary interferometer in optical communication with said external-cavity frequency-tuned laser, said auxiliary interferometer having an auxiliary detector in electrical communication with said processing unit,
   wherein data collected in response to said temporally non-linear frequency sweep are corrected by said processing unit in response to signals from said detector of said auxiliary interferometer.

9. The system of claim 7 wherein said temporally non-linear frequency sweep is sinusoidal.

10. The system of claim 7 wherein data collected in response to said temporally non-linear frequency sweep are corrected by said processing unit in response to signals from said detector.

11. The system of claim 2, wherein said scanner includes a drive mechanism whose drive function is pre-distorted in time to precorrect for any nonlinerarity in the laser transfer function so as to achieve a nearly continuous frequency sweep in time.

12. The system of claim 1 wherein said wavelength selecting device comprises tunable optical filter.

13. The external-cavity laser of claim 12, wherein said wavelength selecting device comprises an AOTF.

* * * * *

UNITED STATES PATENT AND TRADEMARK OFFICE
CERTIFICATE OF CORRECTION

PATENT NO. : 5,956,355
DATED : September 21, 1999
INVENTOR(S) : Swanson et al.

Page 1 of 1

It is certified that error appears in the above-identified patent and that said Letters Patent is hereby corrected as shown below:

Title page,
Box [63] the paragraph under Related U.S.Patent Application should be deleted and replaced with:

-- This application also claims priority under 35 U.S.C. §120 as a continuation -in-part application to copending U.S. Patent Application Serial Number 08/607,787, filed February 27, 1996, which is a continutation-in-part application of U.S. Patent Appliction Serial Number 08/577/366, filed December 22, 1995. now U.S. Patent No. 5,748,598, and is also a continuation-in-part application of U.S. Patent Application Serial Number 08/916,759 filed August 19, 1997 now issued as U.S. Patent No. 5,784,352, which is a FWC application of U.S. Patent Application Serial Number 08/492,738, filed June 21, 1995, now abandoned, and is also a continuation-in-part application of U.S. Patent Application Serial Number 08/252,940 filed June 2, 1994, now abandoned, which is a continuation-in-part of U.S. Patent Application Serial Number 08/033,194, filed March 16, 1993, now U.S. Patent No. 5,459,570, which is a continuation of U.S. Patent Application Serial Number 07/692,877, filed April 29, 1991 now abandoned. --

Signed and Sealed this

Eighteenth Day of September, 2001

*Attest:*

*Attesting Officer*

NICHOLAS P. GODICI
*Acting Director of the United States Patent and Trademark Office*